(12) United States Patent
Makous et al.

(10) Patent No.: US 8,670,833 B2
(45) Date of Patent: Mar. 11, 2014

(54) METHODS AND APPARATUS FOR USING SENSORS WITH A DEEP BRAIN STIMULATION SYSTEM

(75) Inventors: James Makous, Santa Clarita, CA (US); Brett Schleicher, New York, NY (US); Rafael Carbunaru, Valley Village, CA (US); Kristen Jaax, Santa Clarita, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 173 days.

(21) Appl. No.: 12/959,890

(22) Filed: Dec. 3, 2010

(65) Prior Publication Data

US 2011/0137372 A1 Jun. 9, 2011

Related U.S. Application Data

(60) Provisional application No. 61/266,934, filed on Dec. 4, 2009.

(51) Int. Cl.
*A61N 1/00* (2006.01)
(52) U.S. Cl.
USPC ........ 607/54; 607/1; 607/2; 607/53; 600/554; 600/558
(58) Field of Classification Search
USPC ................. 607/1, 2, 53, 54, 45; 600/544, 558
See application file for complete search history.

(56) References Cited

U.S. PATENT DOCUMENTS

| | | | |
|---|---|---|---|
| 6,066,163 A * | 5/2000 | John | 607/45 |
| 6,393,325 B1 | 5/2002 | Mann et al. | |
| 6,539,263 B1 | 3/2003 | Schiff et al. | |
| 6,735,475 B1 | 5/2004 | Whitehurst et al. | |
| 6,819,956 B2 | 11/2004 | DiLorenzo | |
| 6,920,359 B2 | 7/2005 | Meadows et al. | |
| 7,013,177 B1 | 3/2006 | Whitehurst et al. | |
| 7,174,206 B2 | 2/2007 | Frei et al. | |

(Continued)

OTHER PUBLICATIONS

Strecker K, Meixensberger J, Schwarz J, Winkler D., Increase of frequency in deep brain stimulation relieves apraxia of eyelid opening in patients with Parkinson's disease: case report, Neurosurgery. Dec. 2008;63(6):E1204; discussion E1204.*

(Continued)

*Primary Examiner* — Michael Kahelin
*Assistant Examiner* — Mallika D Fairchild
(74) *Attorney, Agent, or Firm* — Vista IP Law Group LLP (57) ABSTRACT

A system and method for applying stimulation to a target stimulation site within a patient, while avoiding undesirable eye movement side effects of the stimulation, are provided. The method includes determining whether eye movement, sensed by internal or external electrodes, is a side effect of a conveyed electrical stimulus. If the eye movement is a side effect, the electrical current distribution of the stimulus is modified in order to steer a locus of the electrical stimulus from one tissue region of the patient to another different tissue region of the patient, thereby mitigating the eye movement side effects. For example, the locus of the electrical stimulus may be steered away from the oculomotor nerve. Eye movement side effects of DBS treatment may include apraxia of lid opening, downward movement and adduction of only one eyeball, and/or continuous deviation of both eyeballs.

21 Claims, 5 Drawing Sheets

(56) References Cited

U.S. PATENT DOCUMENTS

| | | |
|---|---|---|
| 7,206,632 B2 | 4/2007 | King |
| 7,242,984 B2 | 7/2007 | DiLorenzo |
| 7,305,268 B2 | 12/2007 | Gliner et al. |
| 7,324,851 B1 | 1/2008 | DiLorenzo |
| 2008/0071324 A1 | 3/2008 | Miesel et al. |

OTHER PUBLICATIONS

Fawcett, Adrian P. et al., Eye movement-related responses of neurons in human subthalamic nucleus, Exp Brain Res (2005) 162:357-365.

* cited by examiner

METHODS AND APPARATUS FOR USING SENSORS WITH A DEEP BRAIN STIMULATION SYSTEM

RELATED APPLICATION

The present application claims the benefit under 35 U.S.C. §119 to U.S. provisional patent application Ser. No. 61/266,934, filed Dec. 4, 2009. The foregoing application is hereby incorporated by reference into the present application in its entirety.

FIELD OF THE INVENTION

The present inventions relate to apparatus and methods for minimizing eye movement side effects caused by deep brain stimulation.

BACKGROUND OF THE INVENTION

Deep brain stimulation (DBS) and other related procedures involving implantation of electrical stimulation leads within the brain of a patient are increasingly used to treat disorders, such as Parkinson's disease, dystonia, essential tremor, seizure disorders, obesity, depression, restoration of motor control, and other debilitating diseases via electrical stimulation of one or more target sites, including the ventrolateral thalamus, internal segment of globus pallidus, substantia nigra pars reticulate, subthalamic nucleus (STN), or external segment of globus pallidus. DBS has become a prominent treatment option for many disorders, because it is a safe, reversible alternative to lesioning. For example, DBS is the most frequently performed surgical procedure for the treatment of advanced Parkinson's disease. There have been approximately 30,000 patients world-wide that have undergone DBS surgery. Consequently, there is a large population of patients who will benefit from advances in DBS treatment options.

Many of the conditions, diseases and disorders that may be treated with DBS involve irregular brain activity or irregular physiologic activity. For example, tremor activity is associated with Parkinson's disease and other movement disorders. These irregular activities are often indicative of the progression of the condition, disease or disorder.

DBS treatment can also cause side effects. For example, stimulation of the subthalamic nucleus may cause eye movements due to the stimulation spreading to fibers of the oculomotor nerve. An increase in irregular eye movement may be a side effect of over-treatment or may indicate that the stimulation is not being applied to the correct target area.

In current DBS treatment schemes, the parameters of stimulation are set for a patient and remain unchanged for a predetermined amount of time. However, a patient's symptoms may change within that predetermined amount of time, thus subjecting the patient to periods of over-treatment and/or under-treatment. In addition, side effects experienced by the patient may change over time.

Thus, closed-loop DBS systems have been developed, or at least conceived, wherein stimulation parameters are adjusted in response to a sensed condition. For example, a positive closed-loop DBS system may be configured for sensing seizure or tremor activity using, e.g., EEG, and for applying stimulation energy in order to prevent or mitigate the seizure or tremor activity. In another example, a DBS system may be configured for sensing eyelid movement using, e.g., EMG, and for adjusting stimulation parameters in order to provide optimal control of irregular eyelid movement. When operating DBS systems (whether closed-loop or open-loop) within patients, the same stimulation used to efficaciously treat the neurological disorders from which the patients suffer may also cause side-effects, such as uncontrolled eyeball movement.

There, thus, remains a need for a DBS system that prevents or otherwise mitigates side-effects that may occur during treatment of neurological disorders, while retaining the efficacy of the treatment.

SUMMARY OF THE INVENTION

In accordance with a first aspect of the present inventions, a method for applying stimulation to a target stimulation site within a patient is provided. The target stimulation site may, for example, include brain tissue. The method includes conveying an electrical stimulus to a plurality of electrodes implanted within the patient in accordance with an electrical current distribution. The plurality of electrodes may be carried by two stimulation leads respectively associated with two eyeballs of the patient.

The method also includes sensing eye movement. Sensing the eye movement may include sensing an eyelid movement, a direction of eyeball movement, a speed of eyeball movement, and/or a frequency of eyeball movement. EOG, EMG, internal sensors, and/or dipole movement detection may be used to sense eye movement. The method may also include attaching a sensor directly to one of an ocular muscle and an ocular nerve of the patient, such that the sensing the eye movement may include sensing eyeball movement.

The method further includes determining whether the sensed eye movement is a side effect of the conveyed electrical stimulus. The sensed eye movement may be determined to be a side effect of the conveyed electrical stimulus if the sensed eye movement includes an apraxia of lid opening, a downward movement and adduction of only one eyeball, and/or a continuous deviation of both eyeballs. If the sensed eye movement includes downward movement and adduction of only one eyeball, then the electrical current distribution may only be modified on the stimulation lead associated with the one eyeball. If the sensed eye movement includes continuous deviation of both eyeballs, then the method may further include adjusting an amplitude of the stimulus to reshape a current field of the stimulus.

Still further, the method includes modifying the electrical current distribution if it is determined that the sensed eye movement is a side effect of the conveyed electrical stimulus. Modifying the electrical current distribution may steer a locus of the electrical stimulus from one tissue region of the patient to another different tissue region of the patient. The locus of the electrical stimulus may be steered in a dorsal direction, a lateral direction and/or an anterior direction, and may be steered away from an oculomotor nerve. Modifying the electrical current distribution may include adjusting an electrode configuration of the electrical stimulus by adjusting relative percentages of positive and negative current supplied through active electrodes in the electrode configuration. The electrical stimulus in accordance with the modified electrical current distribution is then conveyed to the plurality of electrodes.

In accordance with a second aspect of the present inventions, a brain stimulation system is provided. The system includes a sensor for sensing eye movement. The sensor may be configured for being implanted internally. Further, the sensor may be configured for being attached directly to one of an ocular muscle and an ocular nerve of a patient, and may be configured for sensing eyeball movement. The sensor may include a dipole movement detection sensor. The sensor may include EOG and/or EMG.

The system also includes a plurality of implantable electrodes, wherein the electrodes are configured for conveying an electrical stimulus in accordance with an electrical current distribution; a stimulation device for generating the electrical stimulus and delivering the electrical stimulus to the electrodes; and a processor coupled to the sensor and the stimulation device, and configured for determining whether the sensed eye movement is a side effect of a conveyed stimulus, and for modifying the electrical current distribution in a manner that minimizes the side effect of the conveyed stimulus. The processor may be configured for determining that the sensed eye movement is a side effect of the conveyed electrical stimulus if the sensed eye movement includes an apraxia of lid opening, a downward movement and adduction of only one eyeball, and/or a continuous deviation of both eyeballs. The processor may be configured for modifying the electrical current distribution in order to steer a locus of the electrical stimulus from one tissue region of a patient to another different tissue region of the patient. The processor may further be configured for adjusting an amplitude of the stimulus in order to reshape a current field of the stimulus.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
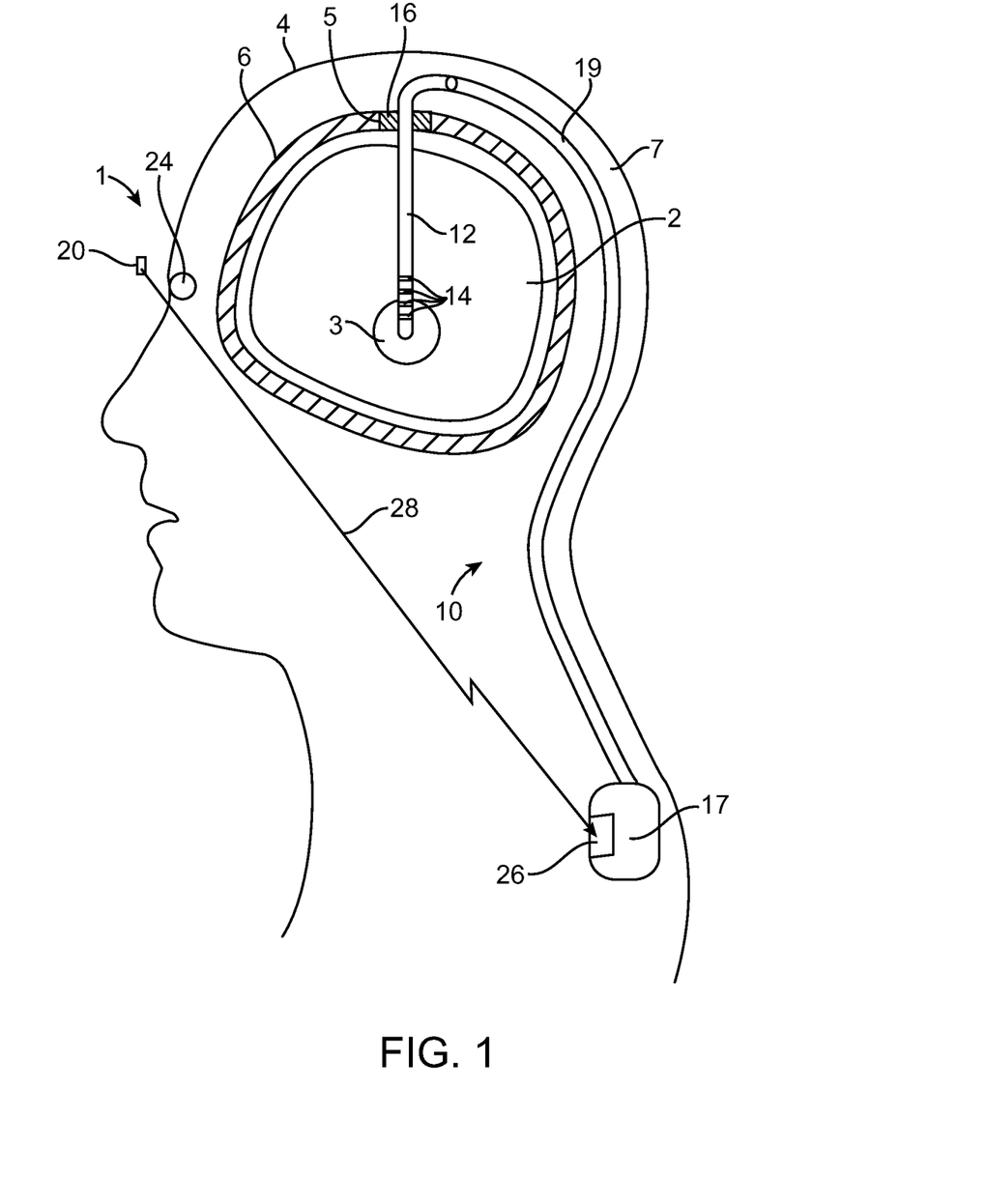
FIG. 1 is a plan view of a Deep Brain Stimulation (DBS) system constructed in accordance with one embodiment of the present inventions, wherein the DBS system is particularly shown implanted within a patient, and wherein the DBS system includes an external sensor.

Turning first to FIG. 1, an exemplary DBS system 10 constructed in accordance with one embodiment of the present inventions is shown implanted within a patient 1 for the treatment of a debilitating disease, such as Parkinson's disease, dystonia, essential tremor, seizure disorders, obesity, depression, etc. The system 10 comprises a stimulation lead 12 implanted within the parenchyma of the brain 2 of the patient 1 in order to position electrodes 14 carried by the distal end of the stimulation lead 12 adjacent a target tissue region 3, such as a deep brain structure of the patient (e.g., the ventrolateral thalamus, internal segment of globus pallidus, substantia nigra pars reticulate, subthalamic nucleus, or external segment of globus pallidus). Thus, electrical stimulation energy can be conveyed from the electrodes 14 to the target tissue region 3 to treat the disease. As can be seen, the stimulation lead 12 is introduced into the head 4 of the patient 1 via a burr hole 5 formed in the cranium 6 of the patient 1 and is secured in place with a burr hole plug 16. The stimulation lead 12 extends from the burr hole 5, through the burr hole plug 16, to a location external to the cranium 6. In alternative embodiments, multiple stimulation leads (not shown) may be used.

The DBS system 10 further comprises a neurostimulator 17, such as an implantable pulse generator (IPG), radio frequency (RF) receiver-stimulator, or any other device coupled to and capable of delivering electrical stimulation energy to the stimulation lead 12 in a controlled and therapeutic manner. The neurostimulator 17 may be generally implanted in a surgically made pocket in the torso of the patient (e.g., the chest or shoulder region). The neurostimulator 17 may, of course, also be implanted in other locations of the patient's body. The DBS system 10 further comprises a lead extension 19, which may be suitably connected to the proximal end of the stimulation lead 12 and subcutaneously advanced underneath the scalp 7 of the patient 1 to the neurostimulator implantation site, thereby facilitating the location of the neurostimulator 17 away from the exit point of the stimulation lead 12 (i.e., the burr hole 5). In alternative embodiments, the neurostimulator 17 may be directly implanted on or within the cranium 6 of the patient 1, as described in U.S. Pat. No. 6,920,359, which is expressly incorporated herein by reference. In this case, the lead extension 19 may not be needed. The system 10 may include external components, such as a patient handheld programmer, a clinician programming station, and an external charger (all not shown), the details of which will not be described herein for purposes of brevity.

After implantation, the neurostimulator 17 is used to provide therapeutic stimulation in a closed-loop or a combined closed-and-open-loop manner. That is, the neurostimulator 17 is configured for generating the electrical stimulus according to one or more stimulation parameters and delivering the electrical stimulus to the electrodes 14. The stimulation parameters may be determined by the neurostimulator 17 or may be determined externally and programmed into the neurostimulator 17. Electrical stimulation energy may be delivered from the neurostimulator 17 to the electrodes 14 using one or more current-controlled sources for providing stimulation pulses of a specified and known current (i.e., current regulated output pulses), or one or more voltage-controlled sources for providing stimulation pulses of a specified and known voltage (i.e., voltage regulated output pulses).

The DBS system 10 also includes a sensor 20 for sensing eye movement. In particular, the sensor 20 may be configured for detecting eyelid movement, direction of eyeball movement, speed of eyeball movement and/or frequency of eyeball movement. As depicted in FIG. 1, the sensor 20 may be external. For example, the sensor 20 may be applied to the patient's skin, attached to eyeglasses or an eye patch (not shown) to be worn by the patient 1, or the like.

Figure 2:
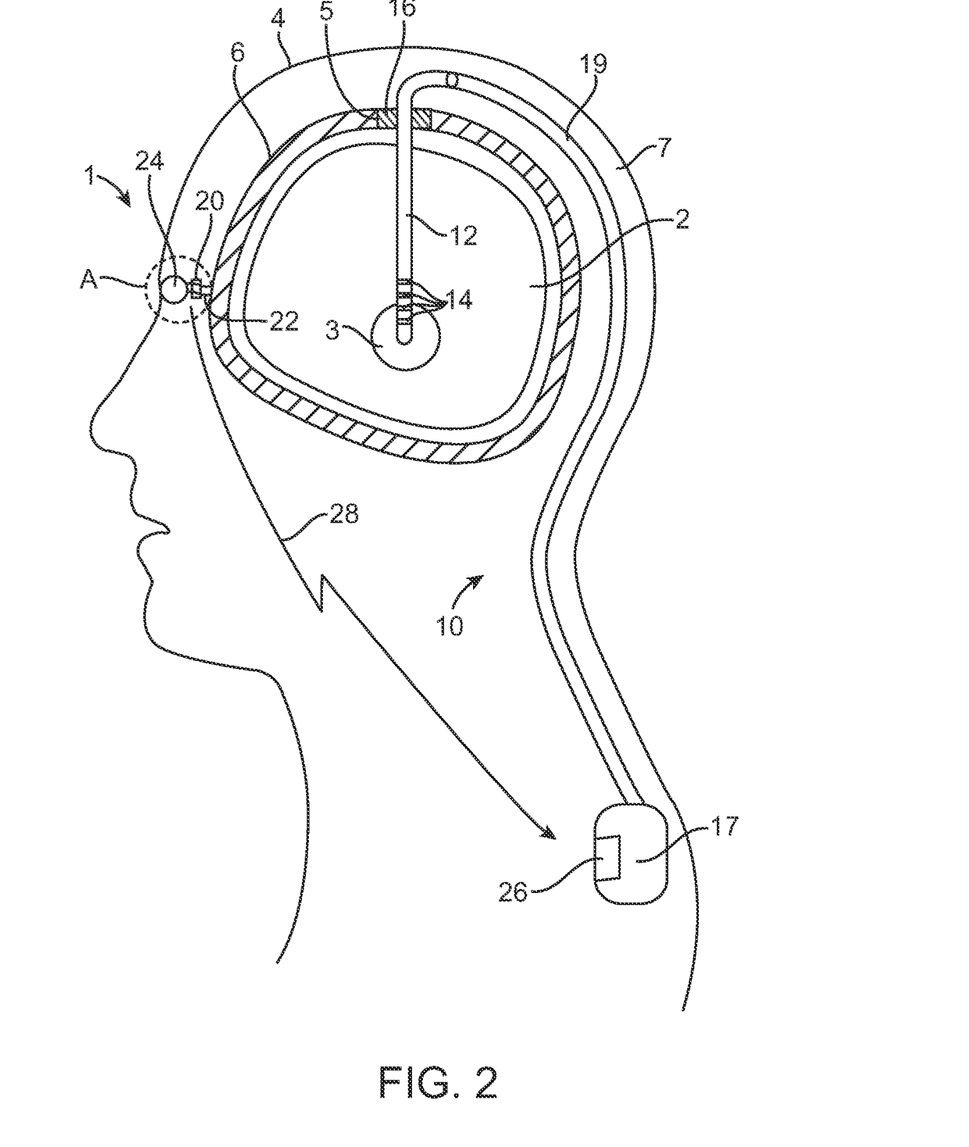
FIG. 2 is a plan view of a Deep Brain Stimulation (DBS) system constructed in accordance with another embodiment of the present inventions, wherein the DBS system is particularly shown implanted within a patient, and wherein the DBS system includes an internal sensor.
Figure 2A:
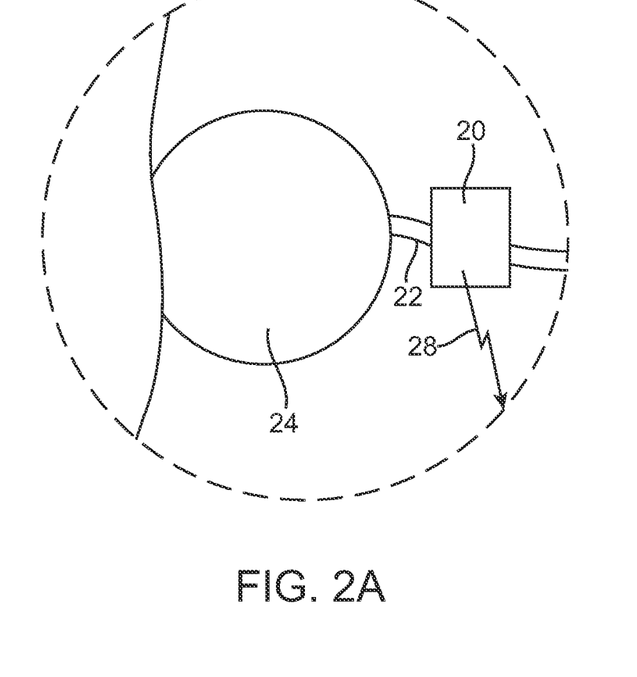
FIG. 2A is a close-up view of an eyeball movement sensor from section 2A in FIG. 2.

Alternatively, as shown in FIGS. 2 and 2A, the sensor 20 may be implanted internally. For example, the sensor 20 may be implanted on, around, and/or near the eyeball 24, muscles of the eyeball, and/or nerves of the eyeball. As shown in FIG. 2A, the sensor 20 may be attached directly to tissue 22 associated with the patient's eyeball 24. The tissue 22 may be a nerve or a muscle that is attached to the eyeball 24. In the embodiment shown in FIG. 2A, the sensor 20 is configured for sensing movement of the eyeball 24 itself. In other embodiments, the DBS system 10 may include more than one sensor, each of which may be internal or external, and may be associated with one of the eyeballs 24.

The sensor 20 may use electromyography (EMG) or electro-oculography (EOG) to detect eye movement. Additionally or alternatively, because the eye is a dipole, eye movement can be detected with surface or implanted electrodes that are configured to detect changes in the dipole. For example, the electrodes 14 on the DBS leads 12 may be used to detect changes in the dipole, and thus, may replace, or be used in addition to, the sensor 20.

The sensor 20 transmits information regarding the eye movement to the stimulator 17. Communication between the sensor 20 and the stimulator 17 may occur wirelessly, as indicted by wireless transmission line 28, or through a hard wired connection (not shown).

The stimulator 17 includes a processor 26 for receiving input from the sensor 20, analyzing the input, e.g., for certain patterns of eye movement, and determining whether the sensed eye movement is a side effect of a stimulus that is conveyed to the target stimulation site 3. If the processor 26 determines that the sensed eye movement is a side effect of the conveyed stimulus, the processor 26 modifies the electrical current distribution of the stimulus in a manner that minimizes the side effects of the conveyed stimulus. In this manner, the locus of the electrical stimulus is steered from one tissue region of the patient 1 to another different tissue region of the patient 1 so that the stimulus may still provide effective treatment and the eye movement side effects are mitigated. Additionally or alternatively, the processor 26 may reshape the current field by decreasing the amplitude.

The electrical current distribution of the stimulus may be modified by varying the distribution of the current/voltage across the electrodes 14, such that the current is supplied via numerous different electrode configurations. In different configurations, different combinations of electrodes 14 may provide current (or voltage) in different relative percentages of positive and negative current (or voltage). Moreover, there may be some electrodes 14 that remain inactive for certain electrode configurations, meaning that no current is applied through the inactive electrode. Even a small change in the electrical current distribution on the active electrodes can change the spatial recruitment of brain tissue, causing a reduction in side effects.

Additionally or alternatively, the electrical current distribution of the stimulus may be modified by changing which electrodes are active in an electrode configuration. That is, the electrical current distribution of the stimulus may be modified by switching one or more of the active electrodes to inactive status and/or by switching one or more of the inactive electrodes to active status. Further details on current steering systems that can be used to modify the electrical current distributions on electrodes are disclosed in U.S. Pat. No. 6,393,325, which is expressly incorporated herein by reference.

Figure 3:
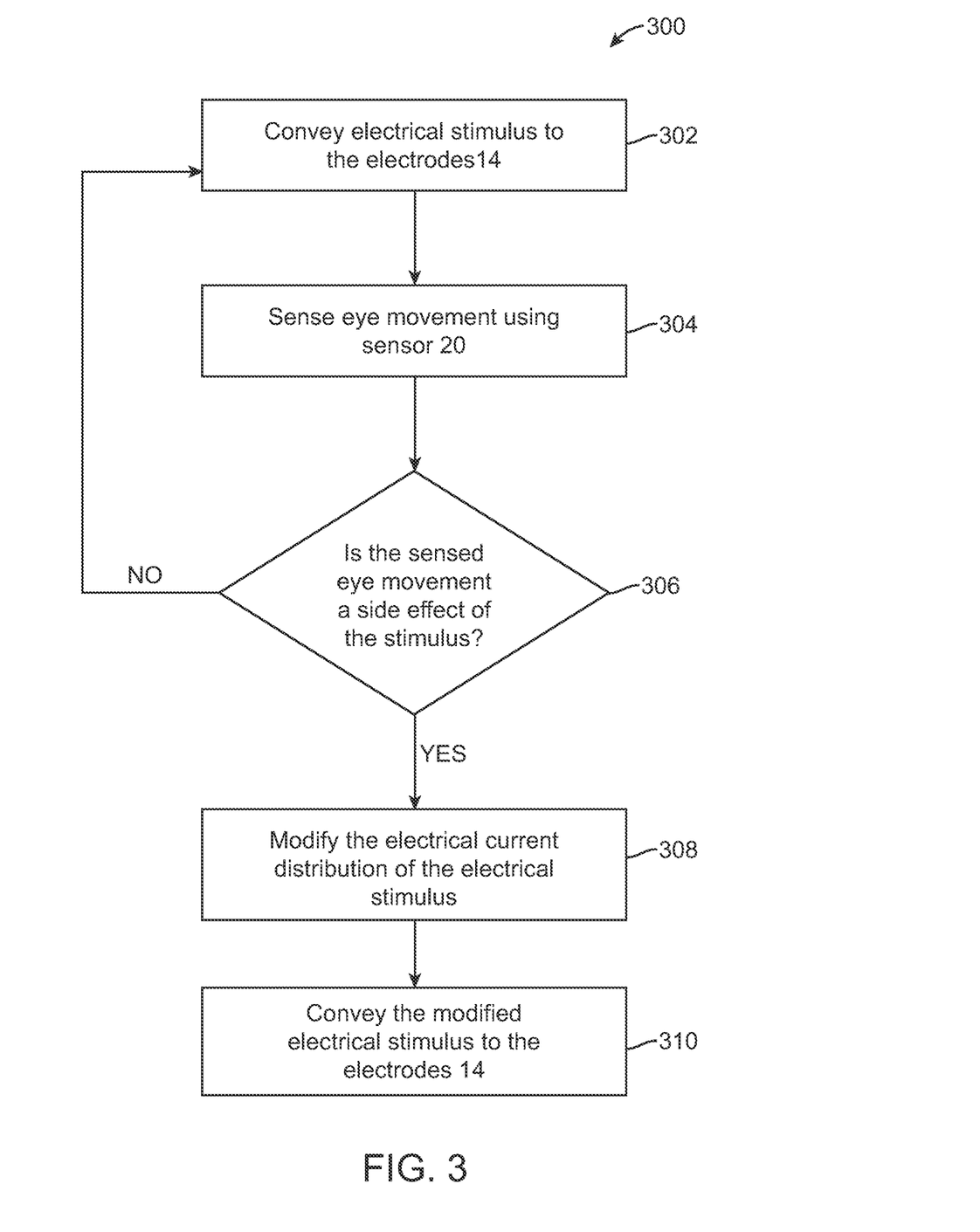
FIG. 3 is a flow chart illustrating a method for applying stimulation to a target stimulation site within a patient while avoiding eye movement side effects of the stimulation.

Referring now to FIG. 3, a method 300 of applying stimulation to a target stimulation site using the DBS system 10 will be described in greater detail. First, in step 302, an electrical stimulus is conveyed to the electrodes 14. The electrical stimulus is defined by a plurality of stimulation parameters, including amplitude, frequency, electrical current distribution, etc.

In step 304, eye movement is sensed using the sensor 20. While step 304 is depicted as occurring after step 302, it should be well understood that eye movement may be sensed continuously, not just after the stimulus is applied. The sensed eye movement is communicated to the processor 26, and, in step 306, the processor 26 analyzes the sensed eye movement to determine whether certain eye movement patterns are occurring. That is, based on the eye movement data, the processor 26 determines whether the patient is experiencing eye movement side effects of the DBS. Eye movement patterns that are side effects of DBS are discussed in more detail in the below examples.

If the processor 26 determines that eye movement side effects are occurring, then, in step 308, the processor 26 modifies the electrical current distribution of the stimulus in order to steer the current and mitigate the side effects. More details regarding the manner in which the electrical current distribution is modified are discussed in the below examples. The electrical stimulus in accordance with the modified electrical current distribution is then conveyed to the electrodes 14 in step 310. If the sensed eye movement is not a side effect of the DBS treatment (i.e., if the "no" path from decision block 306 is followed), then the system 10 continues to convey the un-modified stimulus in an open loop manner, closed loop manner, or combination open-and-closed loop manner.

Example 1

In a first example, an electrical stimulus is conveyed through the electrodes 14 and eye movement is sensed by the sensor 20. Upon analyzing the sensed eye movement, the processor 26 determines that apraxia of lid opening is occurring. Apraxia of lid opening is a side effect of DBS wherein the patient's eyelid is lowered due to inactivity in the levator palpebrae superioris 42, shown in FIG. 4. The levator palpebrae superioris 42 is innervated by the oculomotor nerve, which is controlled by the oculomotor nuclear complex. Trigeminothalamic fibers provide inhibitory input to the central caudal nucleus, a posterior central subnucleus of the oculomotor nuclear complex. Thus, electrical stimulation of trigeminothalamic fibers adjacent to the STN may cause inhibition of the levator palpebrae superioris, resulting in apraxia of lid opening. Thus, in response to the apraxia of lid opening, the processor 26 modifies the electrical current distribution of the stimulus in order to steer the current away from the trigeminothalamic fibers to reduce the inhibition of the levator palpebrae superioris to allow the eye to be opened normally. The current may be steered in the ventral direction to avoid stimulation of the nearby trigeminothalamic fibers. Additionally or alternatively, the processor 26 may reshape the current field by decreasing the amplitude. A stimulus in accordance with the modified electrical current distribution is then applied to the target stimulation site 3 in order to treat the patient 1 (as shown FIG. 1), while avoiding the apraxia of lid opening side effect.

Example 2

Figure 4:
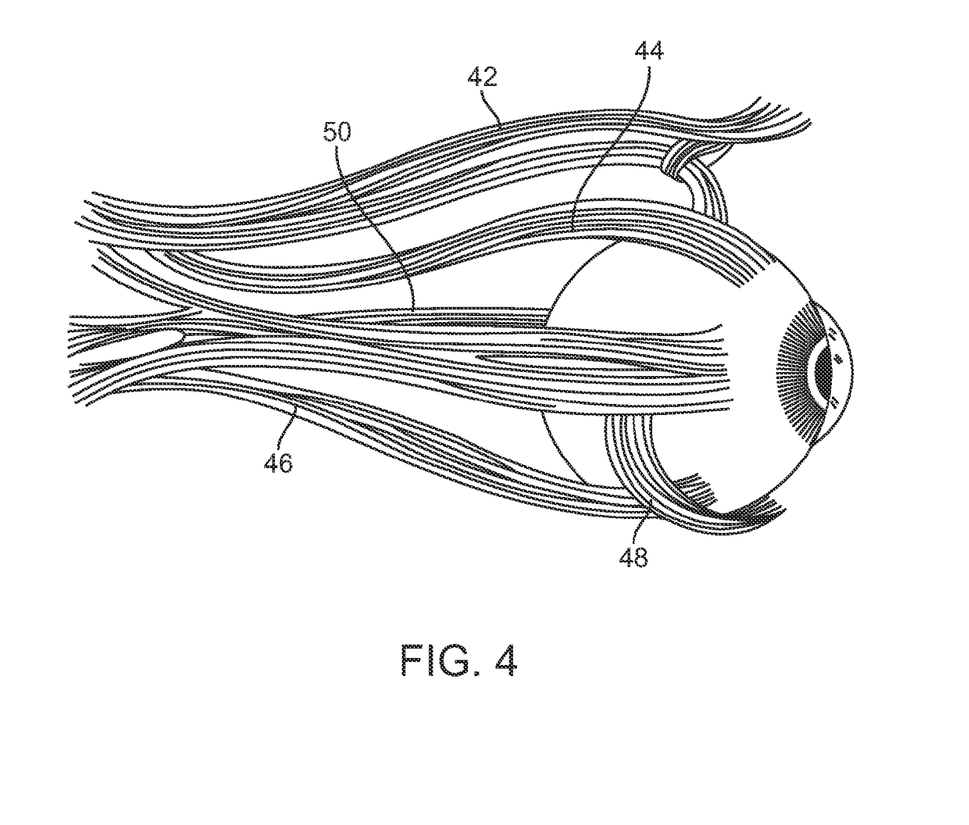
FIG. 4 is a plan view of the muscles of the eye.

In a second example, an electrical stimulus is conveyed through the electrodes 14 and eye movement is sensed by the sensor 20. Upon analyzing the sensed eye movement, the processor 26 determines that downward movement and adduction of only one eyeball is occurring. Such downward movement and adduction of a single eyeball indicates that the superior rectus 44, inferior rectus 46, inferior oblique 48 and medial rectus 50 muscles of the single eye, all of which are depicted in FIG. 4, are being over-stimulated by the DBS treatment. The superior rectus 44, inferior rectus 46, inferior oblique 48 and medial rectus 50 are all innervated by the oculomotor nerve. Thus, in response to the downward movement and adduction of the one eyeball, the processor 26 modifies the electrical current distribution of the electrical stimulus in order to steer the current away from the oculomotor nerve on the lead that is associated with the one eyeball that experiences this side effect. The current may be steered in the dorsal, lateral and/or anterior direction. Additionally or alternatively, the processor 26 may reshape the current field by decreasing the amplitude. A stimulus in accordance with the modified electrical current distribution is then applied to the target stimulation site 3 in order to treat the patient 1 (as shown in FIG. 1), while avoiding the side effect of downward movement and adduction of a single eyeball.

Example 3

In a third example, an electrical stimulus is conveyed through the electrodes 14 and eye movement is sensed by the sensor 20. Upon analyzing the sensed eye movement, the processor 26 determines that continuous deviation of both eyes is occurring. Such continuous deviation of both eyes indicates that the lead 12 is placed too laterally. Thus, in response to the continuous deviation of both eyes, the processor 26 modifies the electrical current distribution of the stimulus in order to steer the current in the dorsal direction, away from the fronto-pontine tract. Additionally or alternatively, the processor 26 may reshape the current field by decreasing the amplitude. A stimulus in accordance with the modified electrical current distribution is then applied to the target stimulation site 3 in order to treat the patient 1 (as shown in FIG. 1), while avoiding the side effect of continuous deviation of both eyes.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for applying stimulation to a target stimulation site within a patient, the method comprising:
   conveying an electrical stimulus to a plurality of electrodes configured to be implanted in the target stimulation site within the patient in accordance with an electrical current distribution;
   sensing eye movement;
   determining whether the sensed eye movement is a side effect of the conveyed electrical stimulus;
   modifying the electrical current distribution when it is determined that the sensed eye movement is a side effect of the conveyed electrical stimulus; and
   conveying the electrical stimulus to the plurality of electrodes in accordance with the modified electrical current distribution.

2. The method of claim 1, wherein sensing the eye movement comprises sensing at least one of an eyelid movement, a direction of eyeball movement, a speed of eyeball movement, and a frequency of eyeball movement.

3. The method of claim 1, wherein the target stimulation site comprises brain tissue.

4. The method of claim 1, wherein modifying the electrical current distribution steers a locus of the electrical stimulus from one tissue region of the patient to another different tissue region of the patient.

5. The method of claim 4, wherein the locus of the electrical stimulus is steered in at least one of a dorsal direction, a lateral direction and an anterior direction.

6. The method of claim 4, wherein the locus of the electrical stimulus is steered away from an oculomotor nerve.

7. The method of claim 1, wherein the sensed eye movement is determined to be a side effect of the conveyed electrical stimulus when the sensed eye movement comprises at least one of an apraxia of lid opening, a downward movement and adduction of only one eyeball, and a continuous deviation of both eyeballs.

8. The method of claim 7, wherein the plurality of electrodes is carried by two stimulation leads respectively associated with two eyeballs of the patient, and wherein, when the sensed eye movement comprises downward movement and adduction of only one eyeball, then the electrical current distribution is only modified on the stimulation lead associated with the one eyeball.

9. The method of claim 7, wherein, when the sensed eye movement comprises continuous deviation of both eyeballs, then the method further comprises adjusting an amplitude of the stimulus to reshape a current field of the stimulus.

10. The method of claim 1, further comprising attaching a sensor directly to one of an ocular muscle and an ocular nerve of the patient, and wherein the sensing the eye movement comprises sensing eyeball movement.

11. The method of claim 1, wherein the sensing the eye movement comprises using at least one of electro-oculography (EOG), electromyography (EMG), internal sensors, and dipole movement detection to sense eye movement.

12. The method of claim 1, wherein modifying the electrical current distribution comprises adjusting an electrode configuration of the electrical stimulus by adjusting relative percentages of positive and negative current supplied through active electrodes in the electrode configuration.

13. The method of claim 1, wherein modifying the electrical current distribution comprises changing which electrodes are active in an electrode configuration.

14. A brain stimulation system, comprising:
   a sensor for sensing eye movement;
   a plurality of implantable electrodes, wherein the electrodes are configured for conveying an electrical stimulus in accordance with an electrical current distribution;
   a stimulation device for generating the electrical stimulus and delivering the electrical stimulus to the electrodes; and
   a processor coupled to the sensor and the stimulation device, and configured for determining whether the sensed eye movement is a side effect of a conveyed stimulus, and for modifying the electrical current distribution in a manner that minimizes the side effect of the conveyed stimulus.

15. The system of claim 14, wherein the sensor is configured for being implanted internally.

16. The system of claim 15, wherein the sensor is configured for being attached directly to one of an ocular muscle and an ocular nerve of a patient, and is configured for sensing eyeball movement.

17. The system of claim 14, wherein the sensor comprises a dipole movement detection sensor.

18. The system of claim 14, wherein the sensor comprises at least one of an electro-oculogram and electromyogram sensor.

19. The system of claim 14, wherein the processor is configured for determining that the sensed eye movement is a side effect of the conveyed electrical stimulus when the sensed eye movement comprises at least one of an apraxia of lid opening, a downward movement and adduction of only one eyeball, and a continuous deviation of both eyeballs.

20. The system of claim 14, wherein the processor is configured for modifying the electrical current distribution in order to steer a locus of the electrical stimulus from one tissue region of a patient to another different tissue region of the patient.

21. The system of claim 20, wherein the processor is further configured for adjusting an amplitude of the stimulus in order to reshape a current field of the stimulus.

\* \* \* \* \*